(12) United States Patent
David et al.

(10) Patent No.: US 9,260,803 B2
(45) Date of Patent: Feb. 16, 2016

(54) METHOD OF ELECTROSPINNING FIBRES

(75) Inventors: William Ian Fraser David, Abingdon (GB); Martin Owen-Jones, Oxford (GB); Derek William Kenneth Jenkins, Chilton (GB); Stephen Bennington, Abingdon (GB); Arthur Lovell, Oxford (GB); Zeynep Kurban, London (GB)

(73) Assignee: THE SCIENCE AND TECHNOLOGY FACILITIES COUNCIL, Oxfordshire (GB)

( * ) Notice: Subject to any disclaimer, the term of this patent is extended or adjusted under 35 U.S.C. 154(b) by 399 days.

(21) Appl. No.: 13/814,709

(22) PCT Filed: Aug. 8, 2011

(86) PCT No.: PCT/GB2011/001185
§ 371 (c)(1),
(2), (4) Date: May 9, 2013

(87) PCT Pub. No.: WO2012/017218
PCT Pub. Date: Sep. 2, 2012

(65) Prior Publication Data
US 2013/0214457 A1    Aug. 22, 2013

(30) Foreign Application Priority Data

Aug. 6, 2010   (GB) .................................. 1013315.5

(51) Int. Cl.
*B29C 44/22* (2006.01)
*B29C 44/24* (2006.01)
(Continued)

(52) U.S. Cl.
CPC . *D01F 8/00* (2013.01); *A61L 15/44* (2013.01); *A61L 27/54* (2013.01); *C01B 3/001* (2013.01);
(Continued)

(58) Field of Classification Search
CPC ...... B29C 44/22; B29C 44/24; D01D 5/0007; D01D 5/0015; D01D 5/0023; D01D 5/003; D01D 5/0038; D01D 5/0046; D01D 5/247; D01D 5/34; D01F 8/04

USPC ........... 264/45.9, 172.15, 209.1, 211.16, 464, 264/465, 466, 484
See application file for complete search history.

(56) References Cited

U.S. PATENT DOCUMENTS

2006/0213829 A1    9/2006  Rutledge et al.
2007/0018361 A1 *  1/2007  Xu ................................ 264/465
(Continued)

FOREIGN PATENT DOCUMENTS

CN    101397372 A    4/2009
CN    101439205 A    5/2009
(Continued)

OTHER PUBLICATIONS

"Instability analysis of a coaxial jet under a radial electric field in the nonequipotential case", Fang Li, Xie-Yua and Xie-Zhen Yin, Phys. of Fluids, 18 (2006) 037101.
(Continued)

*Primary Examiner* — Leo B Tentoni
(74) *Attorney, Agent, or Firm* — Birch, Stewart, Kolasch & Birch, LLP

(57) ABSTRACT

A method of electrospinning fibers is disclosed. The fibers have an inner core surrounded by a porous outer shell. The method comprises co-electrospinning first and second liquids as core and shell respectively, the second liquid surrounding the first liquid in a jet issuing from a Taylor cone, wherein the first and second liquids are miscible or semi-miscible with each other, such that pore generation is driven in the shell of the fiber. The liquids may be solutions or melts. The electrical conductivity, viscosity, miscibility and other parameters of the liquids determine the structure of the produced fibers. As well as producing fibers having a porous shell there are described methods of co-electrospraying porous beads as well as core-shell vesicles having a porous shell. The methods may be used to produce hydrogen storage fibers, vesicles and beads. The methods may also be used for producing controlled drug-delivery fibers, vesicles and beads.

35 Claims, 10 Drawing Sheets

(51) Int. Cl.
*D01D 5/34* (2006.01)
*D01F 8/04* (2006.01)
*D01F 8/00* (2006.01)
*D01D 5/00* (2006.01)
*A61L 15/44* (2006.01)
*A61L 27/54* (2006.01)
*C01B 3/00* (2006.01)
*D01D 5/247* (2006.01)
*H01M 8/04* (2006.01)
*D01D 5/24* (2006.01)

(52) U.S. Cl.
CPC ............. *C01B 3/0026* (2013.01); *C01B 3/0031* (2013.01); *C01B 3/0078* (2013.01); *C01B 3/0084* (2013.01); *D01D 5/0015* (2013.01); *D01D 5/0038* (2013.01); *D01D 5/24* (2013.01); *D01D 5/247* (2013.01); *H01M 8/04216* (2013.01); *A61L 2300/626* (2013.01); *Y02E 60/327* (2013.01); *Y02E 60/50* (2013.01)

(56) References Cited

U.S. PATENT DOCUMENTS

| | | | |
|---|---|---|---|
| 2008/0305377 A1* | 12/2008 | Shui et al. | 264/433 X |
| 2009/0072728 A1* | 3/2009 | Moran-Mirabal et al. | 264/1.27 X |
| 2009/0317446 A1* | 12/2009 | Tan et al. | 424/423 |
| 2010/0047310 A1* | 2/2010 | Chen et al. | 264/465 X |
| 2010/0055154 A1* | 3/2010 | Liao et al. | 264/465 X |
| 2010/0129656 A1* | 5/2010 | Zussman et al. | 264/465 X |

FOREIGN PATENT DOCUMENTS

| | | |
|---|---|---|
| CN | 101789288 A | 7/2010 |
| DE | 3034960 A1 | 4/1982 |
| WO | WO 2008/013713 A2 | 1/2008 |
| WO | WO 2009/151421 A1 | 12/2009 |
| WO | WO 2010/111238 A2 | 9/2010 |

OTHER PUBLICATIONS

Anita Saraf, Genevieve Lozier, Andrea Haesslein, F Kurtis Kasper, Robert M Raphael, L Scott Baggett and Antonios G Mikos: "Fabrication of nonwoven coaxial fiber meshes by electrospinning", Tissue Engineering Part C: Methods; Sep. 2009, Vo. 15, No. 3, pp. 333-344.
Basbouz; "An investigation of yarn spinning from electrospun nanofibres"; PhD thesis, Heriot Watt University, School of textiles and design; May 2009.
Chul Ho Park et al: "One-Step Immobilization of Protien-Encapsulated Core/Shell Particles onto Nanofibres", Macromolecular Materials and Engineering, Wiley VCH Verlag, Weinheim, DE; vol. 295, pp. 544-550; Jan. 1, 2010.
Fan Mei et al: "Morphology Transition in Electrospinning Polymers by a Dual-Capillary System", Journal of Applied Polymer Science, John Wiley & Sons, Inc. US; vol. 115, pp. 204-215; Jan. 1, 2010.
Gutowska, L Li, Y Shin, C M Wang, X S Li, J C Linehan, R S Smith, B D Kay, B Schmid, W Shaw, M Gutowski and T Autrey; "Nanoscaffold mediates hydrogen release and the reactivity of ammonia borane"; Angew Chem. Int. Ed. 44 (2005) 3578-3582.
Jiang H et al; "A facile technique to prepare biodegradable coaxial electrospun nanofibers for controlled release of bioactive agents", Journal of Controlled Release, Elsevier, Amsterdam; NL; vol. 108, No. 2-3, pp. 237-243; Nov. 28, 2005.
Sun Z et al: "Compound Core-Shell Polymer Nanofibers by Co-electrospinning"; Advanced Materials, Wiley VCH Verlag, DE; vol. 15, No. 22, pp. 1929-1932; Nov. 17, 2003.
Zeynep Kurban et al: "A Solution Selection Model for Coaxial Electrospinning and its Application to Nanostructured Hydrogen Storage Materials"; Journal of Physical Chemistry Part C: Nanomaterials and Interfaces, American Chemical Society, US; vol. 114, No. 49, pp. 21201-21213; Dec. 16, 2010.

* cited by examiner (a) (b) (c)

(a)          (b)          (c)

METHOD OF ELECTROSPINNING FIBRES

TECHNICAL FIELD

The present invention relates to a method of electrospinning fibres having an inner core surrounded by an outer shell. The present invention also relates to a method of electrospraying to produce solid or fluid filled vesicles. In particular, the present invention relates to methods of controlling the texture and structure of fibres and vesicles.

BACKGROUND ART

Electrospray is a technique for dispersing a liquid to produce an aerosol. In this technique, a liquid is supplied through a capillary and a high voltage is applied to the tip of the capillary. There is also provided a plate biased at low voltage, such as ground, spaced apart from the capillary in a direction normal to the capillary. The relatively high potential at the tip results in the formation of a Taylor cone. A liquid jet is emitted through the apex of the cone. The jet rapidly forms into droplets as a result of Coulomb repulsion in the jet as shown in FIG. 1.

FIG. 2 shows the related technique of electrospinning. Similarly to electrospray, a voltage source is connected between the tip of a capillary 1 and a collector plate 2. Again, as a result of Coulombic repulsion and surface tension forces a Taylor cone forms. If the liquid is a polymer or other liquid with a viscosity which is high enough (due to high molecular weight), the liquid jet emitted from the Taylor cone does not break up. The jet is further elongated by electrostatic repulsion in the polymer or liquid until a thin fibre is produced. The fibre is finally deposited on the collector 2. Instabilities in the liquid jet and evaporation of solvent can cause the fibre not to be straight and may curl. By careful choice of polymer and solvent system combined with a high enough electric field, fibres with nanometer scale diameters can be formed.

The electrospinning process is a particularly versatile process for the productions of micron-scale fibres and nanofibres. Materials such as polymers, composites, ceramic and metal nanofibres have been fabricated directly or through post-spinning processes. Diameters of 3-1000 nm have been achieved. The fibres produced can be used in a diverse range of fields, from scaffolds for clinical use, to nanofibre mats for sub-micron particulate filtration. Attempts have been made to fabricate more complex fibres, such as fibres having a core material different to an outer shell material, and fibre materials incorporating drugs in the outer shell or bacteria and viruses in the inner core. This process is known as coaxial electrospinning or co-electrospinning.

In prior art co-electrospinning techniques, such as that shown in FIG. 3, a solution 10 to form a core and solution 20 to form a shell are delivered through concentric openings in a nozzle 40. An electric field is applied to the nozzle by a voltage supply 30 to draw the shell solution into a Taylor cone 50 where the electrostatic forces within the surface of the shell solution overcome surface tension forces and a jet 60 issues from the cone. The relative viscosities of the core and shell solutions will also affect the formation of the coaxial jet. Frictional forces such as viscous dragging between the core and shell solutions will cause the core solution to be pulled into the Taylor cone and jet along with the shell solution. Similar to single component electrospinning, a bending instability in the jet will cause the jet to spiral 70. As the jet is drawn to the collector 80, electrostatic forces in the outer surface of the shell fluid will cause the jet to lengthen and thin. Solvents in the core and shell solutions will evaporate so as the jet thins it will begin to solidify into a core-shell fibre. Under continuous operation gram-scale quantities of fibre can be produced rapidly.

Prior art techniques have suggested that the structure of core-shell fibres are influenced by the humidity of the electrospinning environment. However, it would be desirable to provide a method of reliably electrospinning nanotextured core-shell fibres and controlling the texture of electrospun core-shell fibres.

SUMMARY OF THE INVENTION

The present invention provides methods of electrospinning and electropraying core-shell fibres and vesicles, wherein miscible or semi-miscible solutions form a porous shell, and immiscible solutions form a non-porous shell. The shell porosity is controlled by tailoring core and shell liquid miscibilities, in combination with viscosity and conductivity. The present invention also provides methods of electrospinning and electrospraying core-shell fibres and vesicles where the core solution has high conductivity.

The present invention provides a method of manufacturing a fibre, comprising: co-electrospinning first and second liquids as core and shell respectively, the second liquid surrounding the first liquid in a jet issuing from a Taylor cone, wherein the first and second liquids are miscible or semi-miscible with each other, such that pore generation is driven in the shell of the fibre.

The first liquid may have a higher conductivity than the second liquid such that the higher conductivity first liquid drives pore generation in the shell of the fibre.

Each of the first and second liquids may be a molten material or "melt", or a solution comprised of solute dissolved in solvent. Thus, the present invention also provides a method of manufacturing a fibre, comprising: co-electrospinning first and second solutions as core and shell respectively, the second solution surrounding the first solution in a jet issuing from a Taylor cone, wherein the first solution has a higher conductivity than the second solution and the first and second solutions are miscible or semi-miscible with each other, such that the higher conductivity of the first solution of the core drives pore generation in the shell of the fibre. A radial electric field is generated in the solutions. The higher conductivity first solution of the core drives mixing of the solutions in the radial electric field which then drives pore-generation in the shell of the fibre.

Co-electrospinning or co-axial electrospinning is the process whereby at least two fluids are used in a core-shell or core-sheath configuration where the shell or sheath forms an annulus around a circular core cross-section. By conductivity we mean electrolytic conductivity, namely the ability of a liquid (solution or melt) to conduct electricity. By semi-miscible we mean liquids that partly mix but do not fully dissolve in each other. Porosity relates to void spaces in the shell of the fibre, and can mean the fraction of the total volume that is formed of voids. In the present invention the pores are voids having dimensions of around 0.1-0.05 μm to as low as around 0.01 μm diameter when the core-shell fibre is formed. The volume fraction of the shell which is void is at least 5%.

The highly conductive core liquid in the electric field of the electrospinning environment will have charge build up at the interface with the shell liquid. The electrostatic repulsion between the charges may amplify any ripple (capillary waves) on the surface through a field effect, causing them to overcome the surface tension and push out into the shell to create a pore. The pore is created by the amplified capillary waves resulting in core-liquid rich regions protruding into the shell and solidifying or evaporating to leave a pore in the shell.

The invention relates to the combination of the core liquid (solution or melt) having a high conductivity and using semi-miscible or miscible liquids to drive the electrospinning and produce the porous shell. Such a combination of miscibilities and conductivities controls the porosity. In particular, the invention results in the shell having pores which are substantially evenly distributed both longitudinally and azimuthally along the fibre shell. The pores result from instabilities in non-axisymmetric capillary modes at the core-shell interface, which only occur with this combination of conductivities and miscibilities. Prior art methods of fabricating porous fibres have relied on controlling the humidity of the environment and used the standard electrospinning approach of having the higher conductivity solution as the shell. When the core and shell liquids or solution sets are semi-miscible we see porous fibres. When the liquids or solutions are immiscible a largely neat core-shell structure is formed. Certain combinations of miscible solution may also form porous structures.

The present invention also allows electrospinning of polymers or other materials that cannot be electrospun on their own by using a core solution that drives the electrospinning mechanism.

The first liquid may be a solution comprising a first material solvated or dissolved in a first solvent composition and the second liquid may be a solution comprising a second material dissolved or solvated in a second solvent composition. A solvent composition may be a single solvent or a blend of multiple solvents.

When the first liquid is a first solution, and the second liquid is a second solution comprising dissolved polymer, the first and second solutions mix in the cone, or jet, or thereafter, but before solidification, such that the polymer precipitates from the solution mixture.

The method may comprise: supplying the first solution to a core opening in a nozzle; supplying the second solution to one or more shell openings in the nozzle; applying an electric field between the nozzle and a collector to form a fluid cone and fluid jet from the fluid cone, the fluid jet having a core of first solution and shell of second solution; and evaporating the first and second solvent compositions as the jet is drawn towards the collector to produce the fibre.

The fibre may have a porous shell formed from the second material and a core formed from the first material.

The first and/or second solutions may comprise polymer precursors, which form a polymer as the first and/or second solvent evaporates.

The conductivity of the first solution is at least 10 times the conductivity of the second solution, and preferably 100 or 1000 times the conductivity of the second solution.

The second solution has a low conductivity, preferably less than $1 \times 10^{-6}$ S/cm or $1 \times 10^{-7}$ s/cm (for example, at room temperature), such that the electrospinning process is driven by the core.

Shell-core flow rates preferably have a ratio of around 2:1, such as between 1.7:1 and 2.3:1.

The method may comprise: selecting the first and second solvent compositions by calculating Hansen-solubility parameters to determine the solubility of the first material in the first solvent composition and the solubility of the second material in the second solvent composition; and comparing the Hansen-solubility parameters for the first and second solvent compositions to determine if the first and second solvent compositions are miscible or semi-miscible with each other.

The step of selecting may comprise calculating the radius of the solubility sphere Ra for the first or second solvent and determining if this is less than the radius of interaction R0 for the first or second material. The determination takes place between Ra and R0 of the first solution, and between Ra and R0 of the second solution.

The first solution may be considered miscible or semi-miscible with the second solution if the relative energy difference (RED) is less than or equal to one, wherein the relative energy difference is the radius of the Hansen solubility sphere for the two solutions divided by the radius of interaction for the first or second solution.

The first and/or second solvents may be formed of a blend of two or more base solvents. By base solvent we mean a single solvent.

The method may comprise increasing the conductivity of the first solution to a predetermined level greater than the conductivity of the second solution by adding a salt to the first solution.

The method may also comprise mixing two or more base solvents to form the first and/or second solution compositions. Such a mixture may have reduced R0 thereby increasing the miscibility of the first and second solutions compositions.

The porous shell of the fibre may comprise a polymer, and the viscosity of the second solution supplied may be set by the amount of polymer dissolved therein.

For electrospinning, the viscosity of the second liquid is preferably greater than the viscosity of the first liquid. Porosity may be promoted by using first and second solutions which have a total viscosity less than 400 cP or preferably less than 300 cP.

The viscosity of the second solution is preferably greater than 100 or more preferably 150 cP, to prevent break up of the jet into electrospray. The viscosity of the first solution is preferably less than 10 cP (or less than 5 cP, such as 1-2 cP) to allow instabilities at the interfacial boundary to grow thereby helping pore generation.

The vapour pressures of the first and second solvent compositions may be within a factor of 2 of each other, or preferably within 50% or 25% of each other.

The pores may have a diameter less than 0.05 μm, or less than 0.01 μm.

The present invention also provides a method of producing a textured fibre, comprising the methods described above, wherein the core is formed from the first material and the porous shell of the fibre is formed from the second material, wherein there is a textured boundary at the core-shell interface provided by the pores, the method further comprising removing the shell to produce a fibre having branches. The branches are projections or protrusions from the core which may for example be bristles or shorter rounded protuberances. The process of removal of the shell may include thermal degradation, sublimation or decomposition depending on the stability and boiling point of the shell. Alternative methods for removing the shell include dissolving, decomposition by UV, or chemical etching. The process of producing a fibre with the shell removed is termed fibre templating.

The textured fibre may have a diameter of 5 μm or less. The branches may have a diameter of 100 nm or less, or 50 nm or less.

The core and porous shell of the fibre produced from the steps prior to heating may comprise polymers, the polymer in the core having a higher carbon number than the shell. By carbon number we mean the number of carbon atoms per molecule of the polymer.

The present invention also provides a method of producing a porous hollow fibre by removing the core of a core-shell fibre electrospun according to the above methods. The core may be removed by dissolving after electrospinning, or the core fluid may evaporate during spinning. For example, the core may comprise a solvent that evaporates during spinning. The shell includes pores obtained as described above and provides the texturing of the shell.

The present invention also provides a method of producing a hydrogen storage fibre, comprising the methods described above for preparing a core-shell fibre, wherein the first material is a hydride and the second material is a polymer or polymer precursor, and the produced fibre has a porous polymer shell with a hydride core.

The hydride may be ammonia borane (AB) and the polymer may be polystyrene. The shell may be permeable to hydrogen but non-permeable to borazine and borazine type compounds.

The present invention also provides a method of manufacturing a controlled pharmaceutical-drug release fibre, the method comprising the steps described above, wherein the first material comprises a pharmaceutical drug and the second material is a polymer or polymer precursor, and the produced fibre has a porous polymer shell with a core containing a pharmaceutical drug.

The present invention further provides a method of manufacturing a wound dressing or tissue scaffold comprising the method described for manufacturing a pharmaceutical drug release fibre, and further comprising weaving the fibres to form the wound dressing or tissue scaffold.

The present invention also provides method of electrospraying vesicles or beads using the techniques described above, but with lower viscosity than for electrospinning.

The present invention also provides a method of electrospraying vesicles having a porous shell surrounding a core, the method comprising: supplying a first solution to a core opening in a nozzle, the first solution comprising a first material dissolved in a first solvent composition; supplying a second solution to one or more shell openings in the nozzle, the second solution comprising a second material dissolved in a second solvent composition; applying an electric field between the nozzle and a collector to form a fluid cone and fluid jet from the fluid cone, the fluid jet having a core of first solution and shell of second solution surrounding the first solution, the jet breaking up into vesicles; evaporating at least the second solvent compositions as the vesicles are drawn towards the collector to produce vesicles having a shell formed from the second material and a core formed from the first material, wherein the first solution has a higher conductivity than the second solution and the first and second solutions are miscible or semi-miscible with each other, such that the higher conductivity first solution of the core drives pore generation in the shell of the vesicles. The vesicles may have a solid or liquid core. Vesicles may also be produced using melt-electrospinning.

The present invention provides a method of producing hydrogen storage vesicles, comprising the method of electrospraying vesicles described above, wherein the first material is a hydride and the second material is a polymer or polymer precursor, and the produced vesicles have a porous polymer shell with a hydride core.

The present invention also provides a method of manufacturing controlled drug release vesicles, comprising the steps above for electrospraying vesicles, wherein the first material comprises a pharmaceutical drug and the second material is a polymer or polymer precursor, and the produced vesicles have a porous polymer shell with a core containing a pharmaceutical drug.

The present invention provides a method of electrospraying porous beads, comprising co-electrospraying first and second liquids as core and shell respectively, the second liquid surrounding the first liquid in a jet issuing from a Taylor cone, wherein the first and second liquids are miscible or semi-miscible with each other, such that mixing of the liquids in the jet, or in droplets formed from the jet, drives pore generation through the bead. For the jet from the Taylor cone to break into droplets to electrospray instead of electrospin, the liquids must have lower viscosity than that used for electrospinning. The liquids may be solutions. The second liquid may be a solution comprising a dissolved polymer or polymer precursor, and the liquids mix causing separation of the polymer from solution to drive pore generation. In the case of electrospraying the pores may be generated throughout the beads due to the lower viscosities required for electrospray. As a result the distinction between core and shell in the produced bead or vesicle may be lost. In this way hydrogen storage beads or pharmaceutical-drug controlled release beads may be made. Hydrogen storage beads may comprise a matrix of pores, the matrix comprised of polymer and the pores containing hydrogen storage material such as hydride.

The present invention provides a method of manufacturing a fibre having a shell surrounding a core, the method comprising: co-electrospinning first and second liquids as core and shell respectively, the second liquid surrounding the first liquid in a jet issuing from a Taylor cone, wherein the first liquid has a higher conductivity than the second liquid, and the first and second liquids are immiscible with each other, such that no mixing of the first and second liquids occurs at the interfacial boundary thereby producing a fibre having a non-porous shell.

The viscosity of the second liquid may be greater than the viscosity of the first liquid.

The viscosity of the second liquid is no more than three times the viscosity of the first liquid. This prevents instabilities growing and thereby stops pores forming.

The viscosity of the second liquid maybe in the range of 150-600 cP, or more preferably 150-500 cP, or even 180-250 cP.

The conductivity of the first liquid may be at least 10 times greater than the conductivity of the second liquid.

The first liquid may be a first solution comprising a first material dissolved in a first solvent composition. The second liquid may be a second solution comprising a second material dissolved in a second solvent composition.

The step of co-electrospinning may comprise: supplying the first liquid to a core opening in a nozzle; supplying the second liquid to one or more shell openings in the nozzle; applying an electric field between the nozzle and a collector to form a fluid cone and fluid jet from the fluid cone, the fluid jet having a core of first liquid and shell of second liquid; and drying the first and second liquids as the jet is drawn towards the collector to produce the fibre, wherein the step of drying comprises evaporating the first solvent composition or cooling the first liquid below its melting point, and evaporating the second solvent composition or cooling the second liquid below its melting point.

The method may comprise selecting the first solvent composition by calculating Hansen-solubility parameters to determine the solubility of the first material in the first solvent composition. The method may further comprise selecting the second solvent composition by calculating Hansen-solubility parameters to determine the solubility of the second material in the second solvent composition.

The Hansen solubility parameters may be determined for the first and second liquids to determine if they are immiscible.

The step of comparing may comprise calculating the radius of the solubility sphere Ra for the first and second liquid, and determining if this is greater than the radius of interaction R0 for the first or second liquid.

The first liquid maybe considered immiscible with the second liquid if the relative energy difference (RED) is greater than one, wherein the relative energy difference is the distance between the centres of the Hansen solubility spheres for the two liquids divided by the radius of interaction for the first or second liquid.

The present invention provides a method of producing a hydrogen storage fibre, comprising the method described above, wherein the first liquid comprises a hydride and the second liquid comprises a polymer or polymer precursor, and the produced fibre has a non-porous polymer shell with a hydride core.

Preferably, the polymer is permeable to hydrogen and impermeable to larger modules such as borazine, borazine type compounds, ammonia and oxygen. The hydride may be ammonia borane (AB) and the polymer polystyrene. The hydride may be an alanate, alane, an amide-hydride compound, a borohydride, or a metal amido-borane, such as: a) a compound of one of magnesium amide, lithium amide, and sodium amide, with one of magnesium hydride and lithium aluminium hydride; b) lithium borohydride, magnesium borohydride, sodium borohydride, potassium borohydride or beryllium borohydride; or c) lithium amidoborane, sodium amidoborane, a calcium amidoborane, or an aluminium amidoborane. Suitable alanates are sodium alanate or titanium-doped lithium alanates. The polymer may be one of: polysulphone, poly-(vinyl acetate), poly-(benzimidazole), poly-(styrene-co-butadiene), polyvinylidene fluoride, polyvinyl pyrrolidone, polyethylene glycol, polyamide, poly(isobutylene), poly(vinyl alcohol), and SEBS (polystyrene-block-poly(ethylene-ran-butylene)-block-polystyrene).

In summary, core-shell fibres with a porous shell may be electrospun from a core solution having a viscosity as low as 1-2 cP, when the core and shell solutions or liquids are semi-miscible, and the core is highly conducting.

Core-shell fibres with no porosity on the shell are formed when the core solution viscosity approaches that of the shell.

Electrospraying is prevented at shell viscosities of around 180-250 cP or greater.

In any of the above embodiments, the viscosity of the first and/or second solution may be set to the desired level by adding polymer. An example of a suitable polymer is PEO.

BRIEF DESCRIPTION OF THE DRAWINGS

Embodiments of the present invention, along with aspects of the prior art, will now be described with reference to the accompanying drawings, of which:

FIGS. 12a-12b show SEM and TEM micrographs of fibres spun from immiscible core-shell solution sets, whereas FIG. 12c shows single phase fibres with ammonia borane crystals attached to the outer surface of the fibres.

DETAILED DESCRIPTION

Figure 1:
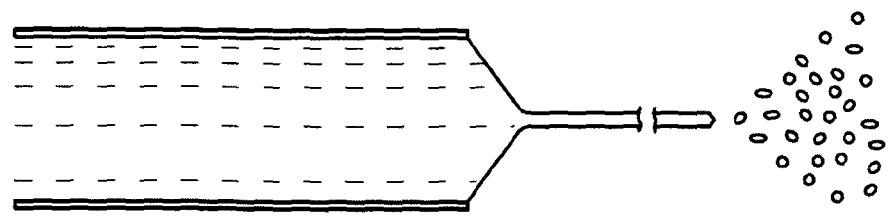
FIG. 1 is a schematic diagram of electrospray from a capillary tube.
Figure 2:
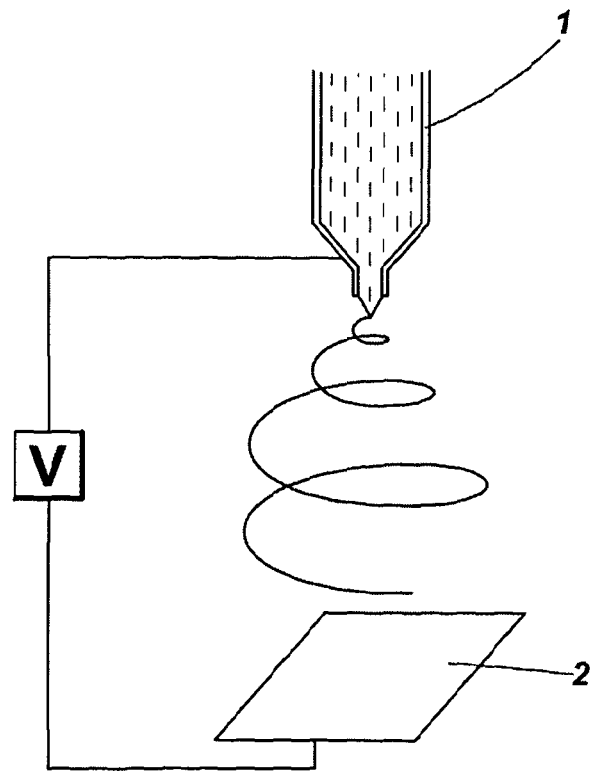
FIG. 2 is a schematic diagram of a conventional single component electrospinning apparatus.
Figure 3:
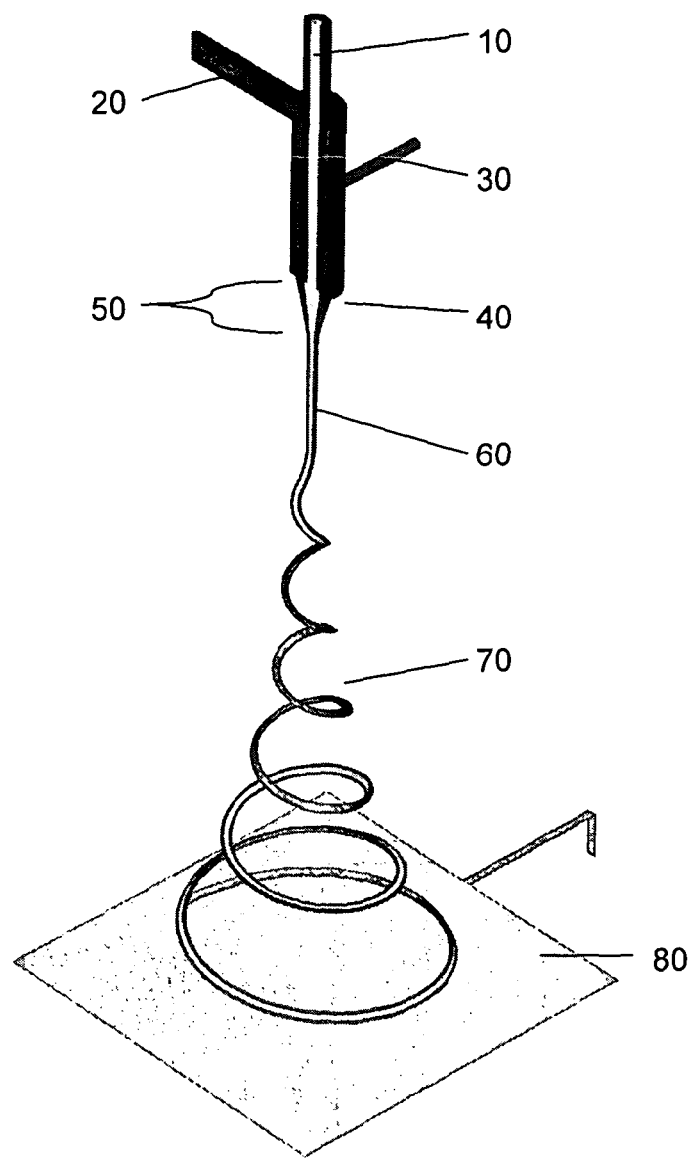
FIG. 3 is a part cut-away schematic illustration of apparatus for co-electrospinning of a core-shell fibre.
Figure 4:
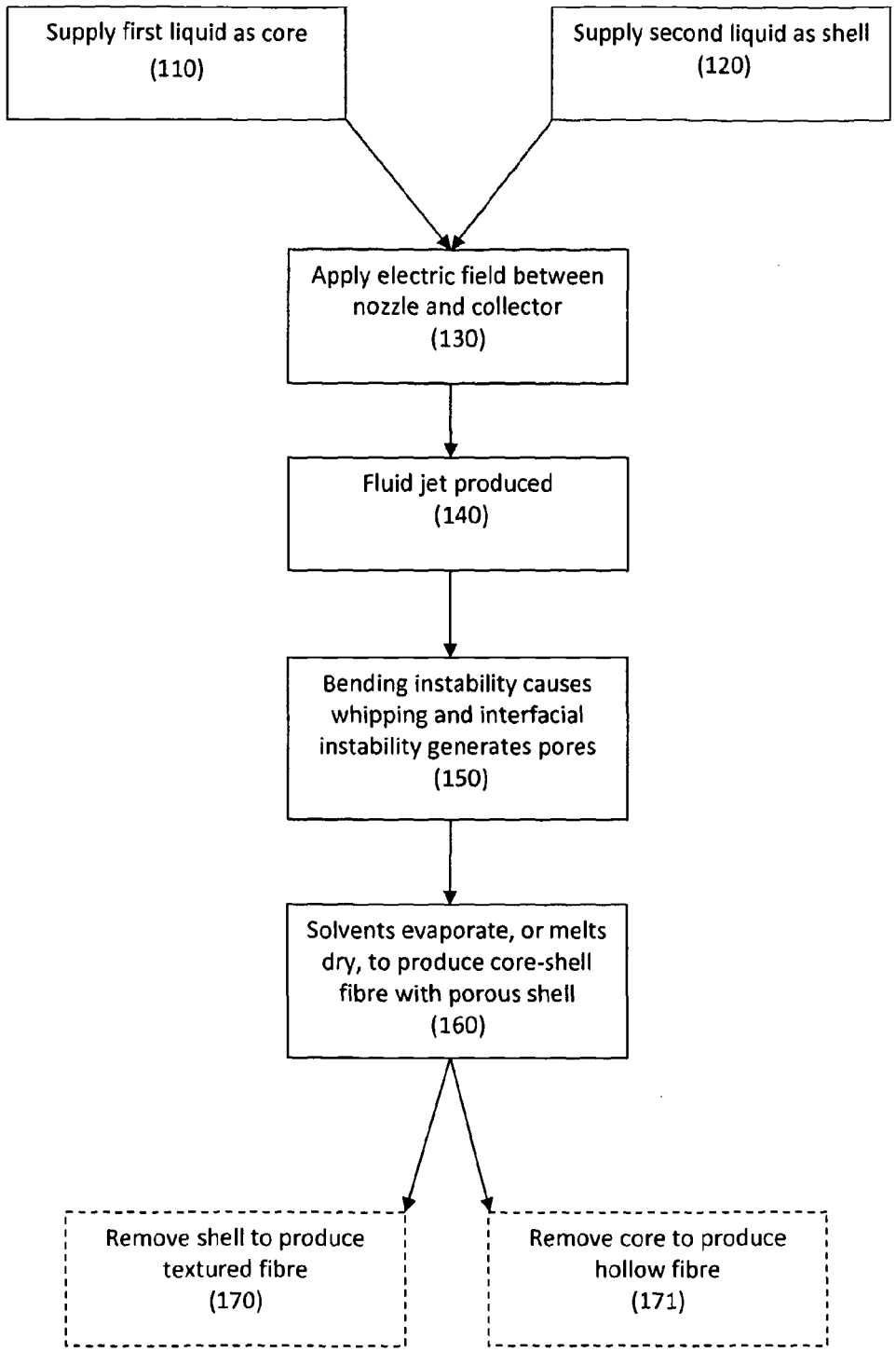
FIG. 4 is a flow diagram describing the steps of co-electrospinning.

FIG. 4 is a flow chart showing steps of manufacturing a fibre according to the present invention. The produced fibre has a core of a first material and shell of a second material different to the first which surrounds the core. FIG. 3 shows the apparatus and arrangement used in the method.

The apparatus comprises reservoirs (not shown) fluidly connected to nozzle 40. The nozzle comprises an inner core channel and an outer concentric annular channel that receive the fluids from the reservoirs. The openings in the nozzle are a central circular one for the core, and an annular concentric opening for the shell. Other shapes and arrangements of openings are available, such as a series of circularly arranged openings for the shell fluid. When the fluid flows through the multiple shell openings the fluid combines to form a shell surrounding the core.

Spaced apart from the nozzle is a collector 80. This may be a conductive plate and may be used to collect the produced fibres. The collector is not limited to being a plate and a further non-conductive surface may be arranged close to the collector between the collector and nozzle to collect the produced fibres. A voltage is applied 130 between the nozzle and collector. This voltage is in the order of kVs to 10s of kV.

A first liquid is supplied 110 comprised of a first material which will form the core of the fibre. A second liquid 120 is supplied comprised of a second material which will form the shell of the fibre The liquids must have favourable miscibilities, viscosities, conductivities, and vapour pressures to allow electrospinning to occur. Selection and setting of these parameters is discussed in detail below.

The first and second liquids are forced through the nozzle under pressure, usually described in terms of flow rates. In conventional co-electrospinning surface tension in the surface of the shell liquid in combination with surface charges in that surface cause a fluid cone (Taylor cone) 50 to form. At the tip of the cone electrostatic forces overcome the surface tension forces and a jet 60 issues 140 from the cone. The Taylor cone and jet are predominantly formed by the shell liquid, with the core liquid being drawn or pulled in to the cone and jet by viscous and frictional forces. In the present invention the core liquid has a higher conductivity than the shell liquid such that the core liquid drives the electrospinning process and allows the texture of the produced fibre shell to be controlled. After ejection from the cone the first and second liquids dry resulting in fibre forming from the fluid jet. As shown in FIG. 3 as the fluid jet or fibre progressively moves towards the collector instabilities in the fluid cause the jet or fibre to bend 150 and may form a spiral or helix 70. Finally after drying of the liquids the solid fibre is formed 160.

Steps 170 and 171 are optional steps, for respectively producing fibres that have a textured surface but no shell, and fibres having no core but a hollow tubular shell. These steps are described in detail later. The first 170 result in the removal of the outer shell, for example, by heating to produce a fibre with an outer surface which may be textured by the presence of pores in the shell. The second 171 results in the removal of the inner core by similar methods to produce a fibre with a hollow core. The resulting shell may be porous or non-porous.

The present invention preferably uses solutions as first and second liquids. However, in some embodiments a "melt" may be used for electrospinning. For example, molten materials may be used as the first liquid and second liquid, or for one of the liquids along with a solution for the other. In such embodiments the molten material or "melt" cools during electrospinning as the jet approaches the collector. When the temperature of the molten material has decreased below its melting point the material solidifies to produce the fibre. The "melt" may form the core or the shell or different "melts" may be used for the core and shell. However, the requirements on viscosity, miscibility, and conductivity are the same as for the preferred embodiment of two solutions.

Returning to the preferred embodiment, the first liquid 10 is a first solution comprising a first material for forming the core of the fibre dissolved in a first solvent. The second liquid 20 is comprised of a second material which will form the shell of the fibre dissolved in a second solvent. The solvent may be comprise a single base solvent or a blend or two or more base solvents. As the jet is ejected from the Taylor cone and moves towards the collector, the solvents in the jet evaporate to produce the fibre.

In the present invention, the liquids used are carefully selected such that the liquid which forms the core of the fibre is of a higher conductivity than that of the second liquid forming the shell. In this case the dominant surface tension and electrostatic forces occur in the first liquid close to the interfacial boundary with the second liquid, that is they occur in the core towards the boundary with the shell. The more highly conducting core is more likely to form a Taylor cone from the competing effects of surface tension and electrostatic forces at the interface. Again at the tip of the cone a jet will issue. The shell liquid will be drawn with the core liquid into the cone and jet by viscous and frictional forces.

As mentioned above there are a number of parameters that must be carefully controlled to allow successful electrospinning of a core-shell fibre having a porous shell.

We now consider in turn control of the various parameters. The parameters are discussed in relation to the preferred embodiment in which the first and second liquids are solutions, but some of these parameters may be readily adapted for the case where the liquids are molten material ("melts") which cool to produce the solid fibre.

Solvent Selection

The Hansen solubility parameters (HSP) are used in understanding and controlling solvent/polymer interactions for optimization of polymer dissolution in solvents. The solubility of materials in solvents depends on entropy and on the nature of the interaction between the solvent and material molecule, such as whether the interactions are mostly dispersive, polar or hydrogen bonded. These interaction strengths are quantified and tabulated for many polymers and solvents as the polar ($\delta_p$), dispersive ($\delta_d$), and hydrogen bonding ($\delta_h$) components of the Hansen solubility parameters in units of $MPa^{1/2}$. These three parameters can be treated as co-ordinates for a point in a three dimensional space, known as the Hansen space, with radius of interaction ($R_0$) for a given solute. $R_0$ is determined empirically as the fourth value in HSP value determination. If the Hansen co-ordinates of a potential solvent (or solvent blend) lie within the solubility sphere of a solute to be dissolved, such as a polymer, then the solvent would be expected to dissolve the polymer, i.e. it will be considered as a good solvent. In order to determine whether this is the case, the distance of the solvent from the centre of the solute solubility sphere ($R_a$) can be calculated using the following equation:

$$R_a^2 = 4(\delta_d^P - \delta_d^s)^2 + (\delta_p^P - \delta_p^s)^2 + (\delta_h^P - \delta_h^s)^2 \quad \text{(Equation 1)}$$

where $\delta_d^s, \delta_p^s$ and $\delta_h^s$ are the HSPs of a given solvent and $\delta_d^P, \delta_p^P$ and $\delta_h^P$ are HSPs of a solute marking the centre of the Hansen solubility sphere. If this distance ($R_a$) is less than the radius of interaction ($R_0$) of the polymer, then the solvent will be expected to dissolve the polymer. The dispersion term is described as being twice as important as the polar- and hydrogen-bonding terms and hence the factor of 4 weighting in the above equation. If this distance ($R_a$) is less than the radius of interaction ($R_0$) of the solute, then it would be expected to dissolve.

A convenient index for the relative ability of a solvent to dissolve a polymer is the ratio $R_a/R_0$, which gives the relative energy difference (RED) of the system: $RED = R_a/R_0$. If $RED < 1$, the molecules are sufficiently alike and the system will dissolve, if $RED \approx 1$ then the system will partially dissolve, and if $RED > 1$ the system will not dissolve, with progressively higher values of RED suggesting progressively more unfavourable interactions. If one does not have an estimate for $R_0$, then solvents can be ranked by $R_a$, with the smaller $R_a$ indicating the better solvents. Since a three dimensional (3-D) graphical presentation is not easy to produce, a more practical method that involves the use of a two dimensional (2-D) plot can be used instead. In this 2-D model the polar ($\delta_p$) and dispersive ($\delta_d$) parameters are combined to give a new parameter $\delta_v = (\delta_d^2 + \delta_p^2)^{1/2}$, which is plotted against $\delta_h$ to produce a two dimensional graphical representation of the solubility parameters. For the 2-D plot the solubility region for a given material is again defined by a circle with a radius $R_0$.

Figure 5:
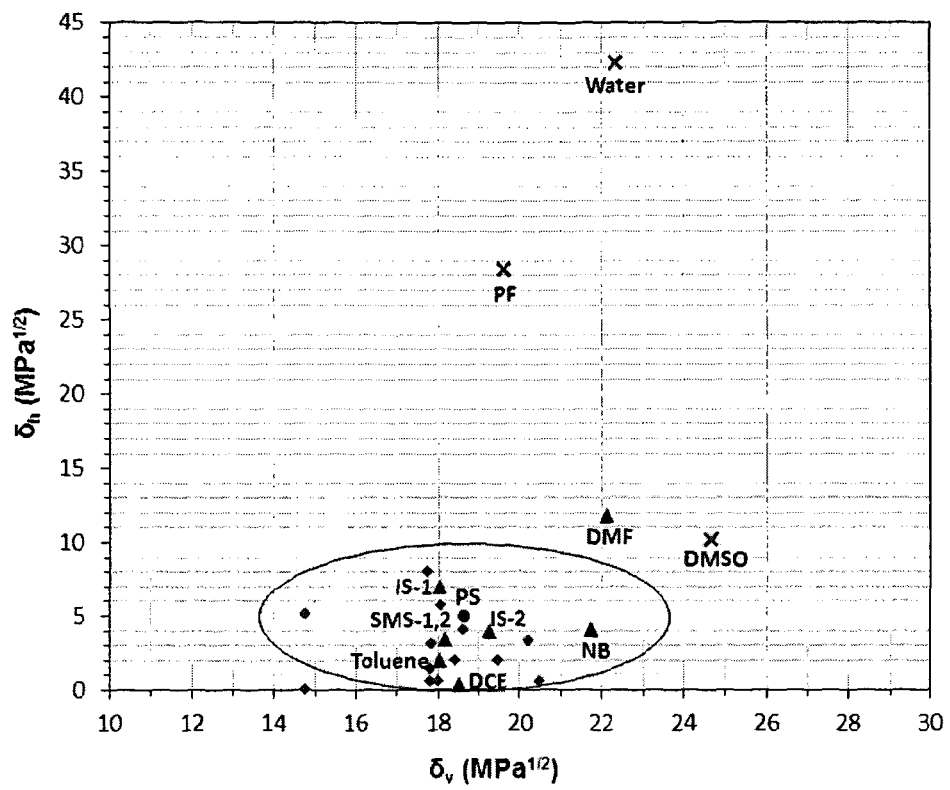
FIG. 5 is a graph of Hansen solubility parameters for polystyrene and various solvents.

FIG. 5 shows a 2-D plot for the polymer polystyrene (PS). The coordinates of the centre of the circle correspond to the solubility parameters $\delta_v = 18$ and $\delta_h = 5$ $(Mpa)^{1/2}$ and $R_0 = 5$. (Note that the circle appears to be elongated due to the difference in axis scale). To identify those solvents that can dissolve polystyrene, the HSPs of a selection of solvents are plotted on the 2-D graph and those that are contained within the Hansen solubility circle are considered as good solvents for polystyrene. This solvent (or solution) selection model, used to predict suitable solvents for a given polymer, has the added advantage of efficiency and increased practicality over other solvent selections methods.

The Hansen solubility parameters can also be used to predict the miscibility of one solvent within another. This is helpful in determining solvents that will mix to form a solvent blend for the core or shell, or to determine whether the core solution and shell solutions will be miscible, semi-miscible, or immiscible. In the latter case the distance apart in Hansen space Ra can be calculated using equation 1 above for the two solvents or solvent blends. The greater the distance apart in Hansen space the less miscible they will be. If the interaction radius R0 for the solvents is known then the RED can be calculated. As described above, if the RED<1, the solvents are sufficiently alike and will be miscible, if RED≈1 then the two solvents will be semi-miscible, and if RED>1 the solvents will be immiscible. If the interaction radius R0 for the solvents is unknown, the distance in Hansen space should be used to assess the miscibility. For example, it is noted that for the solvents discussed below the distance in Hansen space between miscible solvents toluene and DMF is around 16 MPa$^{1/2}$ and the distance between immiscible solvents water and DCE is around 43 MPa$^{1/2}$. This approach can also be used to predict whether one liquid is miscible, semi-miscible, or immiscible with another liquid, such as in the case of melt electrospinning.

Viscosity

Liquid or solution viscosity η, is particularly important for the shell, to provide sufficient shear strength so that the electrostatic forces pull the whole fibre evenly, but also to suppress linear instabilities that would otherwise cause the fibre to break up into droplets or form beaded structures such as in electrospraying. While solution viscosity depends on a combination of factors including average molecular weight of the polymer $M_w$ and polymer concentration, variation of the latter was found to be sufficient to control viscosity due to its exponential dependence on polymer concentration. Polymer can also be added to the core solution to increase its viscosity such that it approaches the shell viscosity thereby decreasing instabilities at the core-shell interface. Combinations of polymers may be used in the core and/or shell to achieve the desired viscosity.

Conductivity

If the material for the core dissolves in solvents that have a low conductivity then the electrospinning will be unlikely to produce a porous shell. To increase the conductivity of the solutions, a blend of solvents may be used. For example, most of the liquids which dissolve polystyrene have very low conductivities. By using a binary or ternary solvent system we were able to selectively change the dielectric constant and hence increase shell-solution conductivity to enable fibre drawing.

Vapour Pressure

If the vapour pressure is too high then the droplet will not be able to make Taylor cone. If the vapour pressure is too low the fibres will deposit wet and form a film on the collector. In co-axial spinning it is usually advantageous to use melts and/or solvents (or solvent blends) with similar vapour pressures in the core and shell to avoid fibre collapse caused by the shell liquid drying more quickly than the core.

Solvent Blends

It is highly unlikely that any two base solvents will have the correct miscibility as well as the conductivity, dielectric constant, viscosity and vapour pressure and ratio of these parameters between the core and shell necessary for co-electrospinning. Thus the further requirements placed on the solvents in order to achieve the desired porosity or non-porosity in the shell will decrease this likelihood further. To overcome this mixtures or blends of solvents are used.

Theory of Pore Generation

We discuss below a theoretical basis for the production of the porous shell in a core-shell fibre, as produced from solutions for the core and shell. A corresponding analysis applies to melt electrospinning.

As mentioned above, by supplying a core solution that has a higher conductivity than the shell solution, the electrospinning and fibre formation is driven by the core material. Furthermore, instabilities in the core-shell boundary make it possible to create highly structured micro- and nano-scale materials. To achieve this the core and shell solutions should:
1) have low interfacial surface tension between the inner and outer fluids;
2) maximize the charge on the interfacial layer by insuring that the inner fluid is much more conducting than the outer; and
3) reduce the viscosity.

We consider two alternatives provided by (3) above. Firstly, if the inner fluid's viscosity is reduced and the outer fluid's viscosity is kept high, instabilities that could cause the break-up of fibre into droplets are suppressed. However, instabilities on the inner surface are still allowed to form and grow. Secondly, if the shell solution, or both core and shell solutions, are inviscid the fibre will break into droplets and electrospraying will occur. If phase separation occurs the beads will be porous throughout and have no distinction between core and shell.

To understand the physical processes that are occurring to create porous structures, we consider the case of a highly conducting core solution and low conductivity shell solution which may be considered to be a leaky dielectric. The driving force on the fibre is largely on the interface between the two fluids and not on the outer sheath, which is more conventional. So this interfacial boundary is where the charge collects.

The interfacial surface tension varies with the miscibility of the two solutions. If the two solutions are identical, i.e. they are miscible, then the interfacial surface tension becomes zero. On the other hand, immiscible solutions must have a significant interfacial surface tension. In the Hansen space the interfacial surface tension is some function of the distance between the two solutions. Capillary waves on this internal surface will become unstable as the surface tension tends to zero. This will become more pronounced under the influence of a strong radial electric field perpendicular to the direction of initial flow. Such a radial electric field results from the fibre, and more specifically the core-shell interface, having an accumulation of charges. During electrospinning this charged fibre is in a region of lower potential and hence a largely radial isotropic field arises around the jet. Ultimately the charges are dissipated when the produced fibre reaches the collector.

To consider capillary waves in the fluid jet we include the surrounding gas or air as a third fluid. The three fluids have fluid velocity, density, viscosity and dielectric constant: $u_i$, $\rho_i$, $\mu_i$ and $\in_i$ where i=c, s, or g for core, shell, and gas respectively. The surface tensions for the two solutions are $\sigma_s$ and $\sigma_c$ and the interfacial surface tension is $\sigma_{sc}$. The waves on the surface of a liquid are called capillary-gravity waves and are described by the equation $$\omega^2 = |k|\left\{\frac{\rho_1 - \rho_2}{\rho_1 + \rho_2}g + \frac{\sigma}{\rho_1 + \rho_2}k^2\right\}$$

where ω is the frequency of the wave, $$k = \frac{2\pi}{\lambda}$$

is the wavevector, $\rho_1$ & $\rho_2$ are the densities of the heavy and light fluids and g is the acceleration due to gravity. The first term is the gravity wave and the second term is the capillary wave. At short wavelength and hence large k, the capillary part of the equation dominates $$\omega^2 = \frac{\sigma}{\rho_1 + \rho_2}|k|^3$$

The amplitude a of these waves depend on the total energy $E_t$ $$a = \sqrt{\frac{E_t}{k\sigma}} \approx \sqrt{\frac{k_B T}{k\sigma}}$$

The surface tension controls both the frequency and the amplitude of the capillary waves. The frequency of these waves are dominated by surface tension between the two solutions. If the solutions have some viscosity then the waves will be damped with a time constant approximately given by:

$$\tau \approx 2k^2 \frac{\rho_1 + \rho_2}{\eta_1 + \eta_2}$$

i.e. the viscosity of either solutions can have a stabilizing effect on the capillary waves.

Applying an electric field to these surfaces turn the capillary waves unstable as the curvature of the surface creates a destabilising force that acts against the damping effects of viscosity or the restoring force of the surface tension.

Previously the complex electrohydrodynamics had been studied only for axisymmetric modes in coaxial fluid fibres, so that the stability conditions under which a jet breaks up into electrospraying have been understood. Before now no work had been done on the stability of non-axisymmetric vibration modes in coaxial fibres such as those which could lead to porosity.

Figure 6:
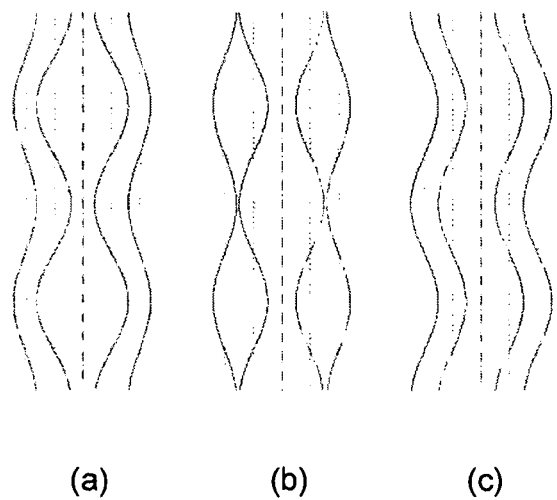
FIGS. 6a-c illustrate axisymmetric bending instabilities that may be found in a coaxial jet.

It is useful to consider the situation for the stability for axisymmetric modes to understand the broad conditions for stability. FIG. 6 shows three axisymmetric instabilities in a coaxial jet. In each figure the core-shell solutions are shown in cross-section such that the core solution is at the central axis, with shell either side. The helical mode, shown in FIG. 6c is the normal spiral or helical mode seen in coaxial spinning that is responsible for the bending and stretching forces that elongate and narrow the fibre. FIGS. 6a and 6b respectively show the parasinuous and paravaricose modes which are responsible for the switch between fibre production and electrospraying. Increasing the viscosity stabilizes the fibre against the parasinuous and paravaricose modes and allows the helical mode to dominate.

To consider the electrohydrodynamics we ignore the viscosities to find an analytical dispersion relation. In the prior art case where the shell is more conducting than the core, the charge is concentrated on the outer shell. The Weber number We which controls the stability is given by $$We = \frac{\rho_s u_s^2 r_s}{\sigma_s}$$

Figure 7:
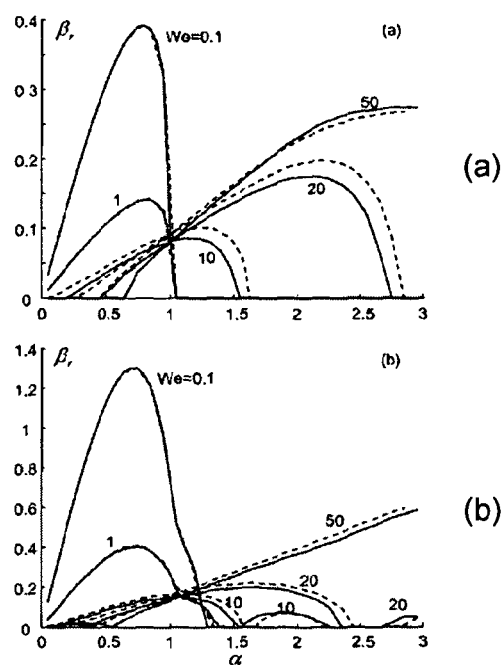
FIGS. 7a and 7b are graphs of wavenumber $\alpha$ versus growth rate $\beta_r$ for different Weber number solutions for parasinuous (FIG. 7a) and paravaricose modes (FIG. 7b)

Variation of growth rate $\beta_r$ versus wavenumber $\alpha$ is shown in FIGS. 7a and 7b. FIG. 7a shows the paravaricose mode, and FIG. 7b shows the parasinuous mode. As the Weber number increases both the modes become unstable at high wavenumbers. (From "Instability analysis of a coaxial jet under a radial electric field in the nonequipotential case. Fang Li, Xie-Yuan and Xie-Zhen Yin, *Phys. of Fluids*, 18 (2006) 037101).

Although non-axisymmetric modes have not been theoretically modelled in detail, high azimuthal number modes are likely to become unstable as the surface tension decreases.

Figure 8:
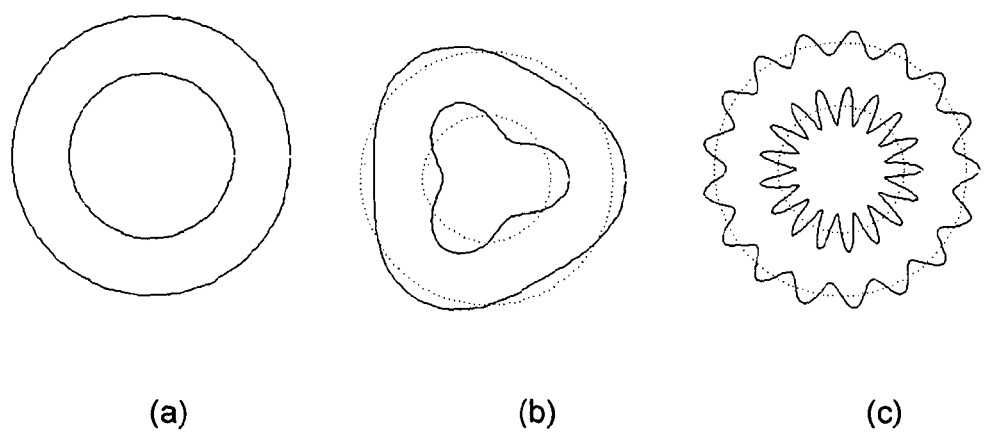
FIGS. 8a-8c schematically show non-axisymmetric modes for a coaxial fibre.
Figure 9:
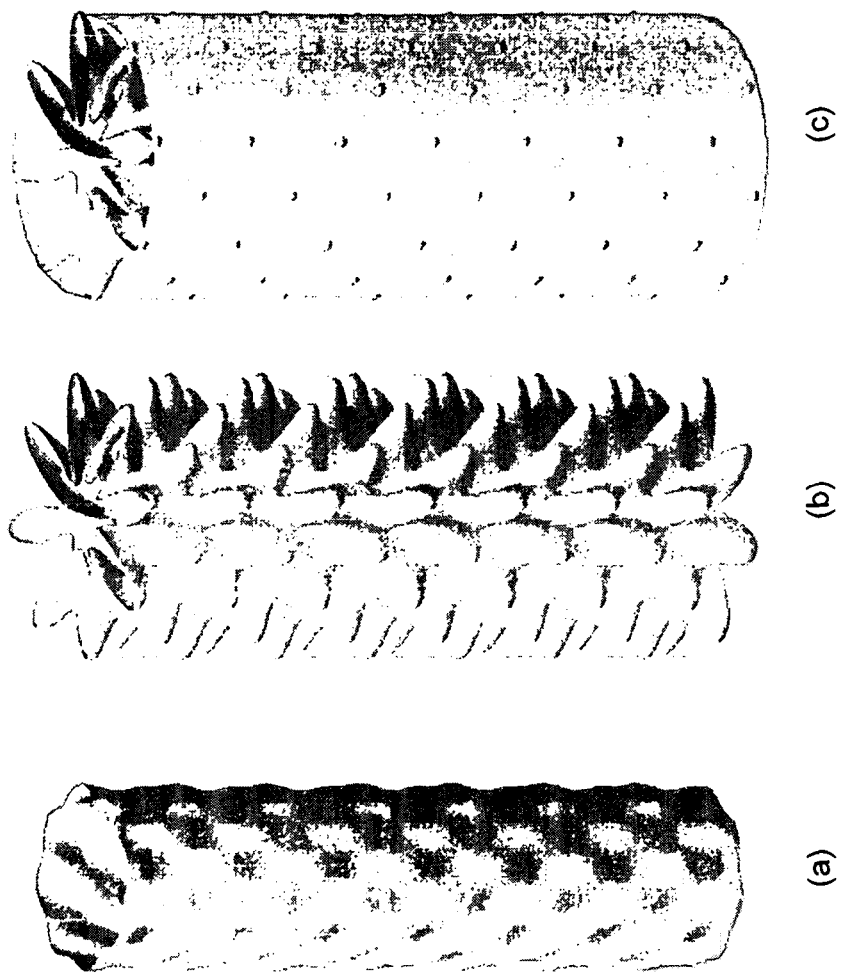
FIGS. 9a-9c show capillary waves with increasing amplitude at the core-shell boundary.

Using a normal mode analysis it is decompose the capillary waves on a cylindrical surface into modes characterised by an azimuthal number m, $$f(r,\theta,z,t) = f(r)e^{\omega t + i(kz + m\theta)}$$

where k is the wavenumber along the fibre. The axisymmetric modes are all m=0 and the helical mode is m=1. FIGS. 8a, 8b, and 8c show non-axisymmetric modes for a coaxial fibre. FIGS. 8a, 8b, and 8c respectively show m=0, m=3, and m=17. FIGS. 9a, 9b, and 9c show capillary waves with m=8 for the interfacial surface with increasing amplitude of the waves. FIGS. 9b and 9c show the capillary waves just breaking through the shell.

These figures are schematic only and it should be remembered that the waves are time varying and it is these waves and their unstable nature that result in pore formation. Conversely from the above analysis we know that the instabilities can be reduced by tailoring the viscosities to suppress capillary waves and that this will prevent pore formation.

It is also thought by the inventors that for the case of polymers in solution for the shell, porosity is caused by viscoelastic phase separation that may occur in mixtures of polymers or mixtures of polymers and solvents. If a polymer is in a poor solvent then as the polymer concentration increases, the Gibbs free energy will force the polymer to pass out of solution either by precipitation from nucleation and growth, or as a continuous spinodal phase separation creating small pockets of solvent rich regions or a continuous network of interconnected pores. The porous nanostructure may be caused by mixing of the core and shell solutions to produce a poor solvent for the polymer such that the mixture separates.

A hydrogen storage application, such as that described below, may use a hydride solution for the core and a polymer solution for the shell. In this case the nanostructure may be produced because the mixture phase separates producing regions rich in hydride solution and regions rich in polymer. As the file dries these separated regions form the porous nanostructure we see. Mixing of the core and shell solutions is encouraged if:

1) the solvents in the core and shell solutions are at least partly miscible to permit mixing;
2) the viscosities of the core and shell solutions are low such that mixing occurs rapidly in the jet;
3) the interfacial surface tension between the core and shell solutions is low; and
4) the higher conductivity in the core solution compared to the shell solution, combined with the radial electric field, drives the mixing.

First Exemplary Application

The method is especially useful for encapsulating materials in porous and non-porous sheaths which can be used to control the release or ingress of liquids and fluids to or from the encapsulated material.

In an embodiment of the invention the method is used to produce a nanostructured fibre to store a fuel. For example, the method can be used to create a safe solid state gas store, storing hydrogen, oxygen or ammonia.

The technique has been verified by encapsulating a hydrogen rich solid such as a hydride as a core material in a polymer shell. In this example, the hydride ammonia borane is used as a core encapsulated in a polystyrene shell.

Ammonia borane (AB) is a waxy solid that contains one of the highest absolute hydrogen densities (19.6 wt %) of any complex hydride. Two thirds of this can be obtained by decomposition at temperatures up to 150° C., which is low compared with other complex hydrides such as alanates. Polystyrene was chosen as the shell material as it has a melting point of 240° C. and so is stable at temperatures of decomposition of the hydride. Polystyrene also has good $H_2$ permeability, at 23.8 barrer, allowing the hydrogen gas to be released. The shell protects the solid while its permeability and porosity allows release of the hydrogen.

It should be noted that permeability is defined as the product of diffusion rate and solubility, and therefore physically different to porosity.

A suitable solvent for dissolving AB was determined by considering the Hansen parameters for a variety of solvents. Although the exact Hansen parameters for AB are unknown, the highly polar nature of AB gives it a strong affinity for solvation in polar solvents, such as water, DMF (dimethylformamide) and DMSO (dimethyl sulfoxide). The HSPs for these three solvents are shown in FIG. 5. These solvents were used in the examples described below to dissolve AB.

To identify solvents that can dissolve polystyrene (PS), the HSPs of a selection of solvents are plotted on the 2-D graph of FIG. 5, as mentioned above. Toluene, nitrobenzene (NB), and dichloroethane (DCE) have HSPs within the circle of solubility for polystyrene. On the other hand water has a very high $\delta_h$ parameter (42.3 Mpa$^{1/2}$) making it a long distance away from the polystyrene solubility circle. Water is therefore expected to be immiscible with those solvents in the circle and a non-solvent for polystyrene. Other possible solvents for dissolving polystyrene are shown in figure by ♦, these include: chloroform, diethyl ether, benzene, ethyl benzene, p-diethyl benzene, tetrahydrofuran, styrene, o-xylene, chlorobenzene, o-dichlorobenzene and carbon disulfide. Any isomer of o-xylene and o-dichlorobenzene could be used, but those in FIG. 5 are the para isomers.

The polar nature of AB makes the conductivity of the AB core solution very high. By adding a salt such as pyridinium formate (PF) to the shell solutions the conductivity of the shell solution was increased. However, the conductivity of the shell solution was never higher than the core solution.

The viscosity of the shell solution was always higher than that for the core due to the long chain nature of polymers. In comparison, the core solution was considered an inviscid liquid.

The vapour pressure is difficult to control and a range of different values were used. One of the solution sets with the most similar vapour pressures was achieved by adding nitrobenzene to the shell solvent. Nitrobenzene has a boiling point of 211° C. and a low vapour pressure.

A number of core-shell solution combinations were trialled for comparative purposes, including miscible, semi-miscible, and immiscible core-shell solutions.

The specific solvent mixtures used to make miscible, semi-miscible and immiscible solution sets are as described below, with the exact combinations summarized in Table 1. For semi-miscible and immiscible solutions sets two alternative core compositions were used for each semi-miscible and immiscible solution. The two alternatives are labelled (a) and (b) in Table 1 and vary the amount of ammonia borane in the solvent.

Miscible

Two miscible solution sets were used: the first (MS-1) used dimethylformamide (DMF) for both the core and shell. The second (MS-2) used dimethyl sulphoxide (DMSO) for the core solvent and DMF for the shell.

Semi-Miscible

By adding DMF to toluene in a 7:1.2 or a 7:1 mass ratio (toluene:DMF) we created solutions with the polystyrene that were semi-miscible with the AB in DMSO (denoted sMS-1 and sMS-2 respectively). The specific shell solvent ratios were chosen to keep the HSPs of the binary mixture within the Hansen sphere. DMF was chosen to improve the dielectric property of the solution to improve the conductivity. The viscosity of sMS-2 was measured at 180-250 cP. Freshly produced solution tended to have a viscosity at the higher end of the range, which reduces as the solution ages because the polymer detangles.

Immiscible

The immiscible sets were made by dissolving the AB in water. To improve the conductivity of the shell, Pyridinium formate (PF) salt, made from equimolar amounts of pyridine and formic acid was dissolved in 1,2-dichloroethane (DCE), a solvent with a high dielectric constant, was added to the toluene. This was used to produce the solution set IS-1 a 3:1:1 volume ratio mixture of toluene:DCE:PF. The viscosity of the IS-1 shell solution was measured to be around 530 cP (530 mPa·s) A second set, IS-2, was similar but used nitrobenzene (NB) to reduce the vapour pressure, in a 7:2:1 volume mixture of DCE:NB:PF. IS-2 was found to have a shell solution viscosity of the same magnitude as IS-1.

The viscosity of the AB core solutions are close to those of water, at 1-2 cP (1-2 mPa·s).

The position of the solution sets sMS-1, sMS-2, IS-1, and IS-2 are marked in FIG. 5.

TABLE 1

| Core-shell solution set | | Shell solution | | Core solution | |
| --- | --- | --- | --- | --- | --- |
| | | Composition | Conductivity at 20° C. (S/cm) | Composition | Conductivity at 20° C. (S/cm) |
| Miscible | MS-1 | 20 wt % PS in DMF | $9.60 \times 10^{-7}$ | 10 wt % AB in DMSO | $1.00 \times 10^{-5}$ |
| | MS-2 | | | 10 wt % AB in DMF | $4.59 \times 10^{-5}$ |
| Semi-Miscible | sMS-1 | 18 wt % PS in 7:1.2 mass ratio Toluene:DMF | $1.00 \times 10^{-8}$ | (b) 20 wt % AB in DMSO | $5.00 \times 10^{-6}$ |
| | sMS-2 | 20 wt % PS in 7:1 mass ratio Toluene:DMF | $1.00 \times 10^{-8}$ | (a) 10 wt % AB in DMSO | $1.00 \times 10^{-6}$ |
| Immiscible | IS-1 | 20 wt % PS in 3:1:1 vol. ratio Toluene:DCE:PF | $4.91 \times 10^{-5}$ | (a) 10 wt % AB in Water | $4.71 \times 10^{-4}$ |
| | | | | (b) 20 wt % AB in Water | $1.13 \times 10^{-3}$ |
| | IS-2 | 20 wt % PS in 7:2:1 vol. ratio DCE:NB:PF | $1.13 \times 10^{-4}$ | 10 wt % AB in Water | $5.72 \times 10^{-4}$ |

The degree of miscibility of the core and shell solvent mixtures were checked experimentally by mixing the shell and core solvents in equal proportions.

Experimental Detail

Ammonia borane ($NH_3BH_3$, AB) complex in powder form and polystyrene (PS) in pellet form were dissolved in the solvents. The solvents used were toluene, N,N-dimethylformamide (DMF), dimethyl sulfoxide (DMSO), 1,2-dichloroethane (DCE), and deionised water. Pyridinium formate (PF), an organic salt, was used to increase the conductivity of some solutions.

The apparatus used is shown schematically in FIG. 3, and has been described above. Further details are now provided. The inner and outer parts of the nozzle 40 were independently connected via tubing to 10 ml syringes on two separate syringe pumps so that the flow rate of each solution could be set independently. Each solution was placed in a co-axial nozzle. The inner diameters of the core and shell nozzles used were 0.5 and 1.5 mm respectively. Syringe pumps were used to push the core and shell solutions through the nozzle inner and outer tubes at the selected flow rates. The flow rate of the core solution was varied between 50 and 500 μl/hr, while that of the shell solution was fixed at 500 μl/hr. An aluminium sheet was used as the collector plate, at a distance of 30 cm from the nozzle tip. A high voltage power supply (from Gamma HV Research Inc.) was used to generate a high DC potential difference across the nozzles (connected to the emitting electrode) and the collector plate (connected to the grounding electrode). The voltages used for the semi-miscible and immiscible solution sets in this study were set at 12 kV and 19 kV respectively. The voltage for each solution set was selected on the basis of stability of the electrospinning process, with these specific voltages yielding the most stable electrospinning. The stability of the spinning process was monitored by a high-speed CCTV camera focused on the nozzle tip.

Figure 10:
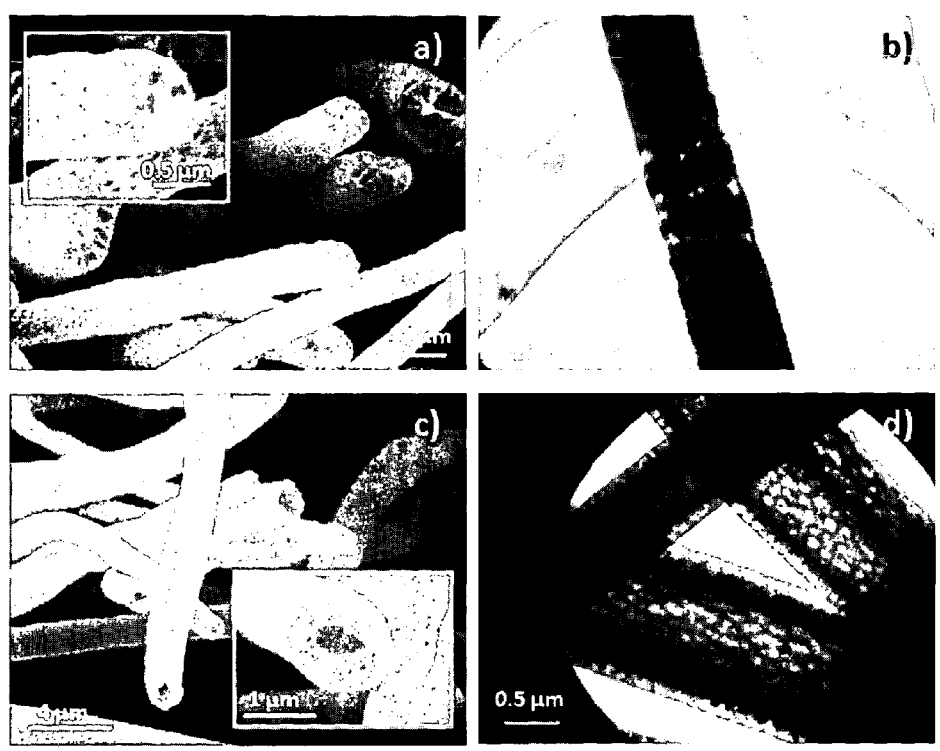
FIGS. 10a-10d are SEM and TEM micrographs of fibres produced from core and shell solutions that are semi-miscible.
Figure 11:
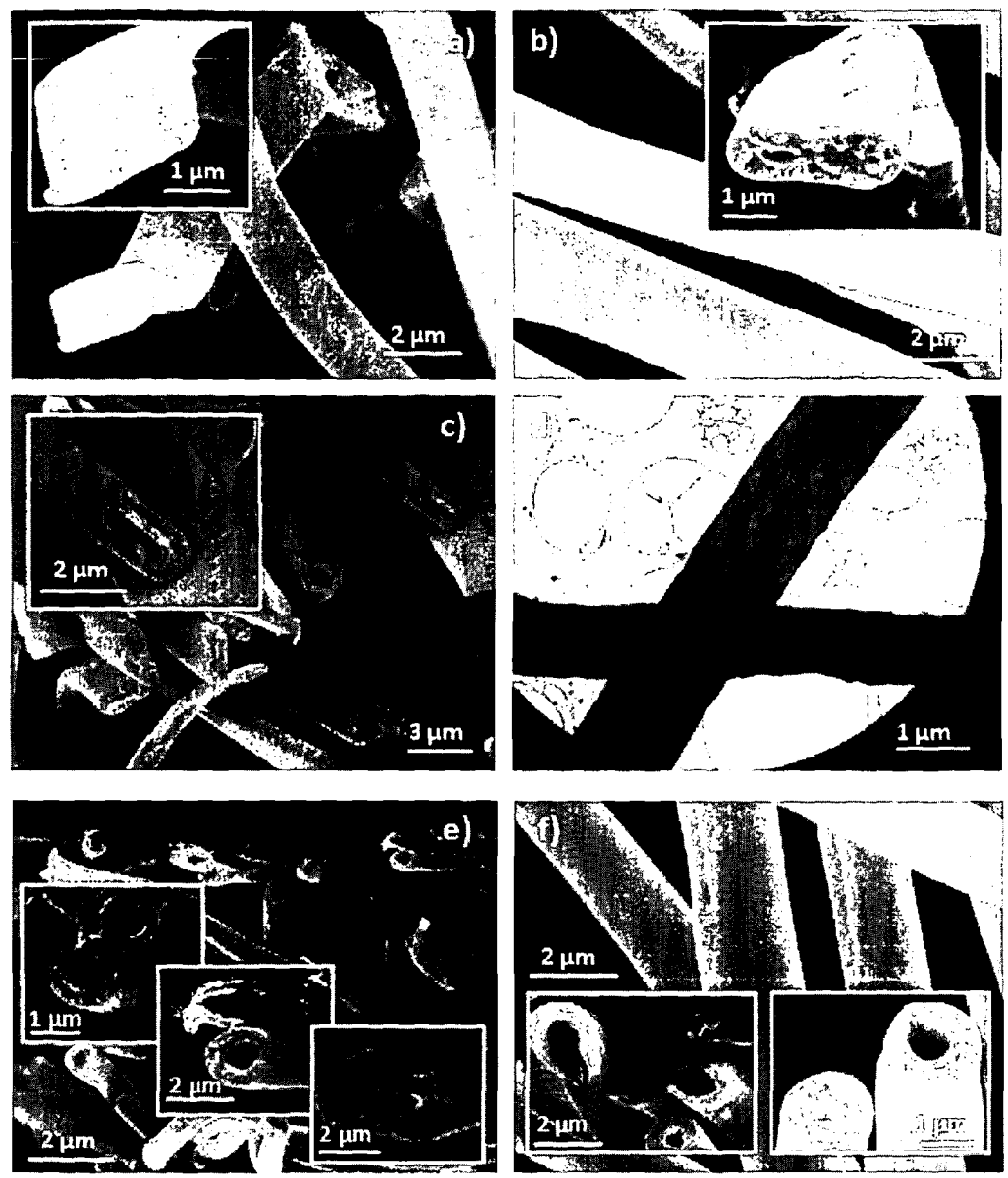
FIGS. 11a-11f are SEM and TEM micrographs of fibres produced from core and shell solutions that are immiscible.

The morphological appearance and the core-shell configuration of the AB-PS fibres are shown in FIGS. 10 and 11. These images were obtained using a field emission scanning electron microscope (SEM, Hitachi S4000) and a transmission electron microscope (TEM, JEOL JEM-2010, $LaB_6$ filament). The latter was used at 200 kV to get a highly magnified and penetrative image of the bulk fibre to ascertain the extent of core-shell structure along the fibre axis.

The dehydrogenation products and mass loss of the co-electrospun AB-PS fibres during thermolysis of the fibres at a heating rate of 1°/min was also analysed. Thermogravimetric analysis of the fibres was conducted using a thermogravimetric analyser (Hiden IGA-001) with in-situ mass spectroscopy.

Significant differences in the fibre morphology and core-shell configuration are seen between solution sets of different miscibility. The extent of decomposition (mass loss) during thermolysis of the fibres also differs depending on solution miscibility.

For all of the fibres discussed here the electrospinning process subjects the polystyrene to large tensile forces, and the resulting structures are set in place by the evaporation of the solvent, leading to a strong orientation dependence in the crystal structure.

Miscible Solution Electrospun Fibres

Co-electrospinning of fibres using the fully miscible solution sets MS-1 and MS-2 was not possible. Although the outer shell solution (20 wt % PS in DMF) can be electrospun successfully on its own, introducing the core solution (10 wt % AB in DMSO or DMF) results in the formation of an elastic gel-like substance at the tip of the nozzle, with the droplet insufficiently liquid to precipitate a jet. This result is attributed to the differing compatibility (or miscibility) of the solvents and solutes; in the case of MS-1, although the core solvent, DMSO, does not dissolve polystyrene, it is highly miscible with the shell solvent DMF. The core solvent appears to mix with the shell solvent producing a solvent mix which can no longer dissolve the polystyrene causing it to aggregate and precipitate out. We also tried using DMF as both the core and shell solvents. The same problem was encountered, although polystyrene precipitated out of the solution at a slower rate. Based on the theory it is expected that a different choice of solvents and materials would successfully result in the productions of fibres from miscible solutions.

Semi-Miscible Solution Electrospun Fibres

The semi-miscible solution sets sMS-1 and sMS-2 were co-electrospun with both 10 and 20 wt % AB in DMSO as the core solution.

FIGS. 10a-10d show SEM and TEM micrographs of fibres co-electrospun using sMS-1 and sMS-2 solution sets. These fibres are highly porous, with the degree of porosity and extent of core-shell configuration changing depending on the particular shell solution concentration and flow rate ratio selected. FIGS. 10a and 10b show SEM and TEM micrographs of the fibres produced using sMS-1 (18 wt % PS in 1:1.2 mass ratio Toluene:DMF) as shell solution, and 10 wt % AB in DMSO as the core solution. These fibres have a high degree of porosity. A pore size of around 0.05-0.1 μm is seen. The core feature is present but small.

FIGS. 10c and 10d show SEM and TEM micrographs of the fibres produced using sMS-2, which has a slightly higher polystyrene concentration with a slightly reduced relative DMF amount. (20 wt % in 7:1 volume ratio Toluene:DMF). These fibres maintain a clear core-shell configuration with a porous sheath structure. The pore size is slightly reduced compared to FIGS. 10a and 10b with a pore size of around 0.05-0.1 μm, to as small as 0.01 μm. For the fibres produced from sMS-1 the pores are spaced approximately 200 nm apart and have an approximately 50 nm opening on the surface of the fibre. The spacing of the pores is roughly the same in directions parallel and perpendicular to the fibre. The shell solution does not electrospin on its own to produce fibres, but it is able to produce fibres when spun co-axially with the highly conducting core solution. Here the charge that collects on the interface between the core and shell drives the electro-spinning of the compound jet. As discussed above, this unusual way of co-axial spinning results in instabilities at the core-shell interface. The build up of charges on the core-shell interface drives the mixing of the two phases with core-solvent rich regions moving into the shell region. The is helped by the low viscosity of the core AB solution. This yields highly porous fibres as shown in FIG. 10.

The fibres shown in FIGS. 10c and 10d were formed at around half the humidity of those of FIGS. 10a and 10b (27% vs 50%). Both sets of fibres shown in these figures show a high degree of porosity.

Prior art methods of producing fibres having porosity have required higher shell conductivity. The method described above is in contrast to these prior techniques as we have used a core with higher conductivity than the shell.

Immiscible Solution Electrospun Fibres

FIGS. 11a-11f show SEM and TEM micrographs of fibres produced using immiscible solution sets. The first immiscible solution set (IS-1) resulted in the formation of mostly collapsed fibres, with some porosity, but with pore size and density significantly lower than that in the fibres produced from sMS. FIGS. 11a-11e show fibres produced from IS-1. On the other hand fibres produced using the second immiscible solution set (IS-2) resulted in nonporous cylindrical fibres with a core-shell configuration and a smooth surface morphology, as shown in FIG. 11f. In prior art literature, fibre porosity is attributed to the atmospheric humidity of the spinning environment where condensation processes leads to the formation of water islands within the fibres causing pore formation. A paper by Casper C L, Stephens J S, Tassi N G, Chase D B, Rabolt J F; "Controlling Surface Morphology of Electrospun Polystyrene Fibers: Effect of Humidity and Molecular Weight in the Electrospinning Process"; Macromolecules; 2003; 37(2); p 573-8; reports that polystyrene fibres tend to have surface features, or pores, when electrospun in an atmosphere with more than 30% relative humidity. The fibres shown in FIGS. 11a-11e were electrospun from IS-1 in an atmosphere with a humidity between 30 and 50%. An increase in porosity with atmospheric humidity is seen compared to fibres produced from sMS. However a large variation in porosity between fibres produced from each solution set (sMS-1, sMS-2, IS-1 and IS-2) is seen even when the fibres are electrospun in an environment with the same atmospheric conditions. This suggests additional factors are influencing the porosity of these fibres. This is clearly illustrated in FIG. 11f which shows fibres spun from the IS-2 set, which have no porosity despite being electrospun in an atmosphere with a relatively high humidity (50%).

Prior art literature also suggests that the vapour pressure of the solvents can affect fibre porosity, with fibres electrospun from solvents of higher vapour pressure having more defined porous structures. This is because in the case of high vapour pressure solvents, when pores are formed due to solvent vaporization and phase separation, the tendency for pores to coalesce is greatly reduced due to a more rapid drying process that leads to a rapid increase in polymer viscosity preventing flow. This could explain why fibres produced from IS-2 are nonporous while those produced from IS-1 have some porosity; the solvent mixture used for IS-2 has a vapour pressure 60% higher than that used for IS-1. It is noted that in the case of fibres produced from sMS-1, while humidity and vapour pressure may affect porosity, the large degree of porosity seen in these fibres (as discussed above) is also attributed to the mixing of core and shell phases under the driving force of the electric field.

The fibres produced from IS-1 are mostly collapsed. Fibre buckling (collapsing) is attributed to the difference in evaporation rates of the core and the shell solvents during the formation of the fibres. The vapour pressure of the shell solvent mixture is approximately 50% higher than that of the core solvent, so the shell solvent will be expected to evaporate first leaving a semi-dry shell layer for the core solvent to diffuse through. The dry skin (shell) layer collapses under atmospheric pressure to form elliptical or flat fibres, the extent of which depends on the diffusion rate of the core solvent through the shell. We find that the degree of collapsing decreases as the core solution flow rate increases for a fixed shell flow rate. This is illustrated in FIGS. 11a-11c which show SEM micrographs of fibres co-electrospun with increasing core flow rates respectively of 150, 250 and 500 μl/hr for a fixed shell flow rate of 500 μl/hr. In the case of fibres co-electrospun using higher core-shell flow rate (350:500 μl/hr) we find a combination of collapsed and non-collapsed fibres, with the larger diameter fibres typically collapsed while the smaller ones more cylindrical, as shown in FIG. 11e. This suggests that the presence of a greater solution (or solvent) volume in the core, as well as reduction of fibre diameters, can reduce the degree of fibre collapse.

Effect of Viscosity on Fibre Morphology

Figure 12:
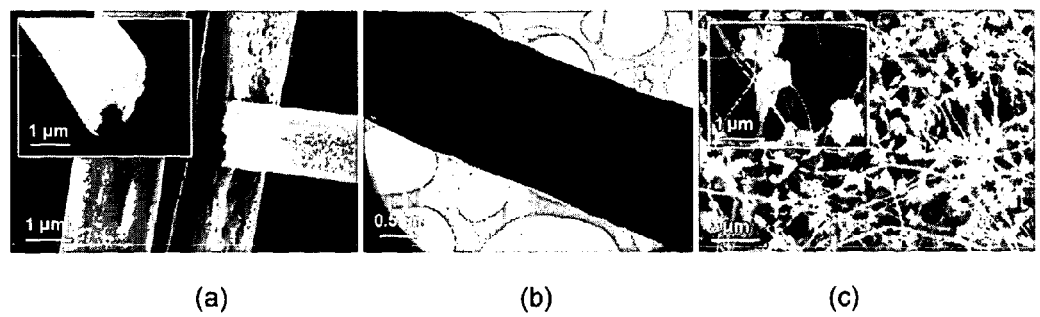

For the co-electrospun fibres described above, the core solution was composed of AB dissolved in a solvent, and due to dissociation of AB ($NH_3BH_3$) molecules in the solvent, the core solution had very low viscosity (1-2 cP) compared to that of the polymeric shell (e.g. 180-250 cP). This satisfies the requirement that the shell viscosity is higher than the core viscosity as required for co-electrospinning. Furthermore, at the voltages of 19 kV used for immiscible solutions, the shell viscosity of 180-250 cP was used to ensure the electrospinning jet did not break up into droplets and turn to electrospray. To test the effect of increasing core viscosity on fibre morphology, without exceeding the value for shell, we added a small fraction (3 wt %) of high molecular weight poly(ethylene oxide) (PEO, Mw=900,000 Da) to the 10 wt % AB-water solution to make the core solution viscous, while keeping the same immiscible shell solution (20 wt % PS in 3:1:1 Toluene: DCE:PF mixture). This increased the core viscosity from 1-2 cP to around 150 cP. Co-electrospinning of this core-shell solution set resulted in the formation of solid fibres where the porosity is largely suppressed and degree of collapse reduced, as illustrated by the SEM and TEM micrographs in FIGS. 12a and 12b. This is consistent with the theory discussed above that suggests viscosity will stabilize the non-axisymmetric modes which cause the porosity. This core solution was electrospun on its own to identify the process parameters that are required for spinning of the core and to test the feasibility of electrospinning a PEO-AB mixture. FIG. 12c shows a micrograph of the fibres obtained from this core solution mixture; due to the low PEO concentration and high solution conductivity ($1.33 \times 10^{-3}$ S/cm) the fibres produced are extremely fine with AB crystals attached to it.

AB-Polystyrene Fibres as a Gas Store

The performance of the AB-polystyrene fibres as hydrogen stores has been assessed by examining the mass-loss of the fibres produced from the semi-miscible solutions (sMS) and the first of the immiscible solutions (IS-1) for different proportions of AB encapsulated in the fibres. AB proportion is given as the product of core solution flow rate and AB concentration used. The mass loss was measured as a function of temperature using thermogravimetric analysis (TGA) at a heating rate of 1°/min. Fibres made from sMS lose significantly more mass at 200° C. than those made from IS-1. The mass loss of sMS increases linearly with AB proportion, with up to 50% mass loss in fibres containing 40% AB. Conversely, the mass loss in fibres produced using IS-1 doesn't vary as significantly for increasing AB content, with approximately 15 wt % mass loss in fibres containing 40% AB. TGA results show that at heating rates of 1° C./min pure AB sublimes. Differential scanning calorimetry (DSC) measurements show that at these low heating rates the material melts at temperatures just below the hydrogen release temperature, so it is likely that vapour pressure is significant.

Any porosity in the fibres will enable the AB to sublime or evaporate at rates similar to that of bulk. The fibres made with immiscible solutions (IS) show much less mass loss, perhaps due to the much reduced porosity, but are still losing more mass than would be expected if only hydrogen was being released.

A paper by Gutowska, L. Li, Y. Shin, C. M. Wang, X. S. Li, J. C. Linehan, R. S. Smith, B. D. kay, B. Schmid, W. Shaw, M. Gutowski and T. Autrey; "Nanoscaffold mediates hydrogen release and the reactivity of ammonia borane"; *Angew Chem. Int. Ed.* 44 (2005) 3578-3582 describes that confining AB in a nano-porous material will reduce the temperature at which the hydrogen is released and suppress the release of borazine. This effect has been attributed to a change in the reaction pathways forced by the confinement in the pores. We see similar effects in the porous fibres where the hydrogen release is reduced in some cases to temperatures as low as 85° C. In contrast the fibres made from the immiscible IS-1 solution set show hydrogen release temperatures that are similar to the bulk, but because of the encapsulation we do not see any significant borazine release. This is because the polystyrene shell is permeable to hydrogen but not permeable to borazine. This is particularly useful for fuel cell applications because the hydrogen can be used to power the fuel cell, while borazine which can poison the cell is not released as with other hydride stores but remains in the encapsulation. The ability to reliably spin non-porous fibres by adjusting miscibilities and viscosities while the core solution has conductivity is significant. Furthermore, the nanostructuring provided by electrospinning improves the thermodynamics of hydrogen release.

Although we have described hydrogen storage fibres using the examples of AB in PS other materials can be used. The encapsulation and release process would work with any complex chemical hydride whose hydrogen release temperature is below the temperature at which the polymer degrades. The hydride must also be soluble in a solvent that is compatible with polymer solvents. Further exemplary materials include: compounds of amides and hydrides (such as of magnesium amide, lithium amide or sodium amide, combined with either lithium hydride, magnesium hydride or lithium aluminium hydride, alanates such as sodium alanate or Ti-catalyzed lithium-alanate, or alane $AlH_3$), borohydrides (such as lithium borohydride, magnesium borohydride, sodium borohydride, potassium borohydride or beryllium borohydride), and metal amidoboranes (such as lithium amidoborane, sodium amidoborane, calcium amidoboranes, and aluminium amidoboranes).

Other polymers could be used which have melting points significantly higher than the hydrogen desorption temperature of the hydride used. For hydrogen storage for a fuel cell, the polymer is preferably permeable to hydrogen and impermeable to any other gasses that the hydride might release such as ammonia or borazine, while also preventing oxygen from penetrating from outside. Such other polymers include: polysulphone, poly(vinyl acetate), poly(benzimidazole), poly(styrene-co-butadiene) Polyvinylidene fluoride, polyvinylpyrrolidone, polyethylene glycol, polyamide, poly(isobutylene), poly(vinyl alcohol), and SEBS (polystyrene-block-poly(ethylene-ran-butylene)-block-polystyrene).

Fibres and Vesicles for Controlled Drug Release

The above described method for producing core-shell fibres and vesicles can be applied to the fabrication of fibres and vesicles for controlled pharmaceutical drug delivery.

By controlling the porosity of the shell it is possible to control the release of drugs for wound dressing or targeted drug delivery. A coaxial fibre with pores in the 100 nm range releases a drug at a slow and controlled rate; and by spinning a drug as the core of the fibre and using a bio-compatible polymer for the shell it is possible to create a fibre that could be used as a scaffold or wound dressing. The fibres are woven or formed into a mat. The fibre mat looks like very fine tissue paper and is made part of the dressing. The fibres can also be used as tissue scaffolds by forming the mat into the desired shape.

Alternatively we could electrospray to create a ~1 μm diameter porous vesicle like structure. In some embodiments the vesicles may become beads which are porous throughout their structure, and unlike the fibres there is less distinction between core and shell in the produced vesicles. The porous vesicle or bead like structure may be created with a bio-degradable polymer encapsulating a drug for injection into the bloodstream or wherever the drug is needed. The outer surface may be coated in an accepter/receptor protein to target the drug more specifically.

This can either be done with bio-degradable polymers such as: Poly(esters) based on polylactide (PLA), polyglycolide (PGA), polycaprolactone (PCL), and their copolymers. Poly (hydroxyalkanoate)s of the PHB-PHV class, additional poly (ester)s, and natural polymers, particularly, modified poly (saccharide)s, e.g., starch, cellulose, and chitosan. Poly (ethylene oxide (PEO) or poly(ethylene glycol) PEG. Or non-degradable but bio-compatible polymers such as ethylene-vinyl acetate copolymer.

Textured Fibre Production

After formation of a fibre with a distinct core and porous shell such as those formed in FIG. 10c, certain combination of core and shell material allow the shell to be removed leaving a fibre having a textured outer surface. The texturing of the fibre is a result of the interface between the core material and the porous shell material.

In one example embodiment the core and shell materials are both polymers. The core polymer has a much higher melting point than the shell polymer. For example PMMA may be used as the shell material, and polyacrylonitrile as the core polymer. By heating the core-shell fibre, step 170 in FIG. 4, to between 300° C. and 400° C. the PMMA decomposes and evaporates as gases leaving the core of the fibre intact. The core has an outer surface that is not smooth but rough. This surface roughness may include branches of 50-100 nm in length where the core material has filled a pore. The material has applications in materials and composite technology.

Other polymers that could be used include PEMA (poly (ethylmethacrylate)) and PPMA (poly(propylmethacrylate)).

Other methods of removing the shell may be used, such as chemical etching or dissolving the shell in a solvent. For these techniques careful selection of chemical etchant or solvent will be required to avoid damage to the fibre.

The opposite process can also be performed in which the core is removed to leave a porous shell. The processes for removal of the core are the same as those discussed above, For example, chemical etching, UV degradation, dissolving the shell in suitable solvent. Alternatively, the shell may have a much higher melting point or degradation temperature than the core, such that the core decomposes leaving the shell intact. As a further alternative the liquid used for the core may evaporate during the electrospinning process to leave the shell. Such liquids may be highly volatile solvents.

The person skilled in the art will readily appreciate that various modifications and alterations may be made to the above described methods without departing from the scope of the appended claims. For example, different materials, melts and solvents may be used. In addition, although the above described embodiments largely relate to electrospinning, these techniques and devices may also be used for electro-spraying.

The invention claimed is:

1. A method of producing a textured fibre, comprising:
  manufacturing a fibre having a porous shell surrounding a core, the manufacturing comprising:
  co-electrospinning first and second liquids as core and shell respectively, the second liquid surrounding the first liquid in a jet issuing from a Taylor cone,
  wherein the first and second liquids are miscible or semi-miscible with each other, such that pore generation is driven in the shell of the fibre,
  wherein there is a textured boundary at the core-shell interface provided by the pores, the method further comprising:
  removing the shell thereby providing a fibre having a surface textured by branches.

2. The method of claim 1, wherein the first liquid has a higher conductivity than the second liquid, such that the higher conductivity first liquid of the core drives pore generation in the shell of the fibre.

3. The method of claim 1, wherein the first liquid is a first solution comprising a first material dissolved in a first solvent composition.

4. The method of claim 1, wherein the second liquid is a second solution comprising a second material dissolved in a second solvent composition.

5. The method of claim 1, wherein the first liquid is a first solution, and the second liquid is a second solution comprising dissolved polymer, and the first and second solutions mix resulting in precipitation of the polymer from the solutions mixture.

6. The method of claim 1 wherein the first and/or second liquid is a melt.

7. The method of claim 1, wherein the step of co-electrospinning comprises:
  supplying the first liquid to a core opening in a nozzle;
  supplying the second liquid to one or more shell openings in the nozzle;
  applying an electric field between the nozzle and a collector to form a fluid cone and fluid jet from the fluid cone, the fluid jet having a core of first liquid and shell of second liquid; and
  drying the first and second liquids as the jet is drawn towards the collector to produce the fibre, wherein the step of drying comprises evaporating the first solvent composition or cooling the first liquid below its melting point, and evaporating the second solvent composition or cooling the second liquid below its melting point.

8. The method of claim 4, wherein the shell is formed from the second material.

9. The method of claim 3, wherein the core is formed from the first material.

10. The method of claim 1, wherein the first and/or second liquids comprise polymer precursors.

11. The method of claim 2, wherein the conductivity of the first liquid is at least 10 times the conductivity of the second liquid.

12. The method of claim 2, wherein the second liquid has a conductivity less than $1 \times 10^{-6}$ S/cm.

13. The method of claim 3, comprising:
  selecting the first solvent composition by calculating Hansen-solubility parameters to determine the solubility of the first material in the first solvent composition.

14. The method of claim 4, comprising:
  selecting the second solvent composition by calculating Hansen-solubility parameters to determine the solubility of the second material in the second solvent composition.

15. The method of claim 1, comprising
  comparing Hansen-solubility parameters for the first and second liquids to determine if the first and second liquids are miscible or semi-miscible with each other.

16. The method of claim 15, wherein the step of comparing comprises calculating the radius of the solubility sphere Ra for the first and second liquid, and determining if this is less than the radius of interaction R0 for the first or second liquid.

17. The method of claim 1, wherein the first liquid is miscible or semi-miscible with the second liquid if the relative energy difference (RED) is less than or equal to one, wherein the relative energy difference is the distance between the centres of the Hansen solubility spheres for the two liquids divided by the radius of interaction for the first or second liquid.

18. The method of claim 1, wherein the first liquid is a first solution comprising a first material dissolved in a first solvent composition, the second liquid is second solution comprising a second material dissolved in a second solvent composition, and the first and/or second solvents are formed of a blend of two or more base solvents.

19. The method of claim 2, wherein the first liquid is a first solution, the method comprising increasing the conductivity of the first solution to a predetermined level greater than the conductivity of the second liquid by adding a salt to the first solution.

20. The method of claim 1, wherein the shell is formed comprising a polymer, and the second liquid is a second solution having a viscosity set by the amount of polymer dissolved therein.

21. The method of claim 1 comprising adding polymer to the first solution to set the viscosity of the first solution.

22. The method of claim 20 wherein the polymer is PEO (polyethelene oxide).

23. The method of claim 1, wherein the viscosity of the second liquid is greater than the viscosity of the first liquid.

24. The method of claim 1, wherein the viscosity of the second solution is greater than 150 cP.

25. The method of claim 1 wherein the viscosity of the first solution is less than 10 cP.

26. The method of claim 1, wherein the vapour pressures of the first and second liquids are within a factor of 2 of each other.

27. The method of claim 1, wherein the pores have a diameter less than 100 nm.

28. The method of claim 1, wherein the textured fibre has a diameter of 5 μm or less.

29. The method of claim 1, wherein the textured fibre has branches with a diameter of 100 nm or less.

30. The method of claim 1, wherein the core and porous shell of the fibre produced from the steps prior to the step of removing comprise polymers, the polymer in the core having a higher carbon number than the shell.

31. A method of producing a hydrogen storage fibre, comprising:
  manufacturing a fibre having a porous shell surrounding a core, the manufacturing comprising:
    co-electrospinning first and second liquids as core and shell respectively, the second liquid surrounding the first liquid in a jet issuing from a Taylor cone,
    wherein the first and second liquids are miscible or semi-miscible with each other, such that pore generation is driven in the shell of the fibre, and
  wherein the first liquid comprises a hydride and the second liquid comprises a polymer or polymer precursor, the produced fibre has a porous polymer shell with a hydride core, and
  wherein the hydride is ammonia borane (AB) and the polymer is polystyrene.

32. A method of producing a hydrogen storage fibre, comprising:
  manufacturing a fibre having a porous shell surrounding a core, the manufacturing comprising:
    co-electrospinning first and second liquids as core and shell respectively, the second liquid surrounding the first liquid in a jet issuing from a Taylor cone, wherein the first and second liquids are miscible or semi-miscible with each other, such that pore generation is driven in the shell of the fibre, and wherein the first liquid comprises a hydride and the second liquid comprises a polymer or polymer precursor, the produced fibre has a porous polymer shell with a hydride core, and wherein the hydride is an amide-hydride compound, a borohydride, or a metal amido-borane.

33. A method of producing a hydrogen storage fibre, comprising:

manufacturing a fibre having a porous shell surrounding a core, the manufacturing comprising:

co-electrospinning first and second liquids as core and shell respectively, the second liquid surrounding the first liquid in a jet issuing from a Taylor cone, wherein the first and second liquids are miscible or semi-miscible with each other, such that pore generation is driven in the shell of the fibre, and wherein the first liquid comprises a hydride and the second liquid comprises a polymer or polymer precursor, the produced fibre has a porous polymer shell with a hydride core, and wherein the hydride comprises at least one of:

a) a compound of one of magnesium amide, lithium amide, and sodium amide, with one of lithium hydride, magnesium hydride, lithium aluminium hydride, lithium alanate, a titanium-doped lithium alanate, sodium alanate, and alane;

b) lithium borohydride, magnesium borohydride, sodium borohydride, potassium borohydride or beryllium borohydride; and c) lithium amidoborane, sodium amidoborane, a calcium amidoborane, or an aluminium amidoborane.

34. A method of producing a hydrogen storage fibre, comprising:

manufacturing a fibre having a porous shell surrounding a core, the manufacturing comprising:

co-electrospinning first and second liquids as core and shell respectively, the second liquid surrounding the first liquid in a jet issuing from a Taylor cone, wherein the first and second liquids are miscible or semi-miscible with each other, such that pore generation is driven in the shell of the fibre, and wherein the first liquid comprises a hydride and the second liquid comprises a polymer or polymer precursor, the produced fibre has a porous polymer shell with a hydride core, and wherein the polymer is one of: polysulphone, poly-(vinyl acetate), poly-(benzimidazole), poly-(styrene-co-butadiene), polyvinylidene fluoride, polyvinylpyrrolidone, polyethylene glycol, polyamide, poly(isobutylene), poly(vinyl alcohol), PMMA, PEMA, PPMA, PAN and SEBS (polystyrene-block-poly(ethylene-ran-butylene)-block-polystyrene).

35. The method of claim 21, wherein the polymer is PEO (polyethelene oxide).

* * * * *